United States Patent [19]

Zudkevitch et al.

[11] 4,428,798

[45] Jan. 31, 1984

[54] EXTRACTION AND/OR EXTRACTIVE DISTILLATION OF LOW MOLECULAR WEIGHT ALCOHOLS FROM AQUEOUS SOLUTIONS

[75] Inventors: David Zudkevitch, Denville; Stephen E. Belsky, Morris Plains; Preston D. Krautheim, Blairstown, all of N.J.

[73] Assignee: Allied Corporation, Morris Township, Morris County, N.J.

[21] Appl. No.: 401,793

[22] Filed: Jul. 26, 1982

[51] Int. Cl.[3] .................. B01D 3/40; C07C 29/84; C07C 29/86
[52] U.S. Cl. ................................ 203/18; 203/19; 203/65; 203/73; 203/78; 203/84; 568/918
[58] Field of Search ............ 203/18, 19, 65, DIG. 13, 203/73, 78, 84, 43-46, DIG. 13; 568/916, 918

[56] References Cited

U.S. PATENT DOCUMENTS

| | | | |
|---|---|---|---|
| 2,486,342 | 10/1949 | Taylor et al. | 203/18 |
| 2,583,412 | 1/1952 | Carlson et al. | 203/65 |
| 2,695,867 | 11/1954 | Chambers | 203/18 |
| 3,239,434 | 3/1966 | Delaune et al. | 203/65 |
| 3,804,722 | 4/1974 | Oliver | 203/65 |
| 4,306,884 | 12/1981 | Roth | 203/19 |
| 4,379,028 | 4/1983 | Berg | 203/65 |

*Primary Examiner*—Wilbur L. Bascomb, Jr.
*Attorney, Agent, or Firm*—Kenneth E. Stroup, Jr.; Alan M. Doernberg; Gerhard H. Fuchs

[57] ABSTRACT

A process is disclosed for separating low molecular weight alcohols, especially ethanol, from aqueous mixtures. The process involves subjecting alcohol-water mixtures to extraction and/or extractive distillation procedures. Extractive solvents useful for the process of this invention include phenols having at least six carbon atoms and a boiling point between about 180° C. and about 350° C.

16 Claims, 2 Drawing Figures

EXTRACTION AND/OR EXTRACTIVE DISTILLATION OF LOW MOLECULAR WEIGHT ALCOHOLS FROM AQUEOUS SOLUTIONS

DESCRIPTION

BACKGROUND OF THE INVENTION

The present invention relates to a process for separating low molecular weight alcohols from aqueous solutions. It is possible to obtain low molecular weight alcohols having a concentration above about 95% and in many cases above about 99.9% by utilizing the process of this invention. The process is especially suitable for separating ethanol from aqueous solutions.

The concentration or complete recovery of ethanol from aqueous solutions has been accomplished by distillation for many years in the production of alcoholic beverages, solvents and a variety of chemicals. Ethanol from such distillations, either alone or in combination with hydrocarbon fuels such as gasoline, has been more recently used as an automotive fuel. Contamination by residual water is an undesired consequence of most simple fractional distillation schemes. Contamination by residual water is especially undesirable when the alcohol is to be used as fuel.

Extraction of aqueous ethanol solutions by organic solvents has been previously proposed. In these proposals, the extract containing both ethanol and solvent is generally distilled to separate the product ethanol and a recycle solvent. An article by J. W. Roddy, entitled "Distribution of Ethanol-Water Mixtures to Organic Liquids" in Ind. Eng. Chem. Process Des. Dev., volume 20, pp 104–108 (1981) indicates that a wide variety of organic solvents have been used for such extractions, but that the number of solvents having distribution coefficients greater than 0.5 for ethanol and separation factors greater than 10 from aqueous solutions (as defined in the Roddy article) are quite limited. The article indicates the general order of extraction for ethanol to be hydrocarbon=halocarbon<ether<ketone<amine<ester<alcohol=phosphate.

The best candidate identified in the article was 2-ethyl-1-butanol, which had a distribution coefficient of 0.69 for ethanol and a separation factor of 30. The next best candidate, tri-isobutyl phosphate, had a distribution factor for ethanol of 0.65 and a separation factor of 10. The solvents that are proposed in the present invention have distribution coefficients of 1.1 or even larger for ethanol.

It has also been proposed to conduct a distillation to separate ethanol from water with an additional solvent being added to the system so as to either enhance the separation and purity of ethanol as the overhead and of water as the bottoms, or to reverse the volatilities for ethanol and water, causing water to be removed as top product, and ethanol mixed with solvent to be removed as bottom product. Examples of such suggestions are contained in U.S. Pat. No. 2,591,672 (with a hydrocarbon as the extractive distillation solvent) and an article by C. Black entitled "Distillalation Modeling of Ethanol Recovery and Dehydration Process for Ethanol and Gasohol", in Chem. Eng. Prog., September 1980, pp 78–85, especially at pp 82–84. It has also been proposed in an article by S.A. Leeper and P. Wankat, in Industrial and Engineering Chemistry Process Design and Development, April 1982, pp 331–334 to extract alcohol from an aqueous solution with gasoline. However, this process requires concentrating the alcohol in the feed stream to a 90% level prior to the extraction. Also, said process produces only gasohol, a mixture of gasoline and alcohol, and does not produce pure alcohol.

Copending Application Ser. No. 276,302 (Zudkevitch et al., 1981), and now-abandoned discloses a process for the separation of ethanol from aqueous solutions by reversing the relative volatility between ethanol and water. In the Zudkevitch et al. procedure and in the procedures discussed by Black, the ethanol/water, ethanol/solvent and solvent/water binaries all exhibit positive deviations from ideal mixing. Positive deviations from ideal mixing for the solvent/alcohol binary are less desirable than negative deviations when extraction of the alcohol is considered, because said positive deviations are accompanied by repulsive forces between the alcohol and the solvent. Thus, separation of the alochol from water by extraction or extractive distillation is more difficult when the alcohol/solvent binary exhibits a positive deviation from ideal mixing. On the other hand, in the process proposed herein, separation of alcohols from aqueous solutions is facilitated when the water/solvent binary exhibits a positive deviation from ideal mixing.

While the above references indicate the desirability of extraction, extractive distillation and azeotropic distillation schemes to recover ethanol from aqueous solutions, a need exists for solvents suitable for carrying out the desired separation with higher selectivities than those proposed heretofore. We have discovered a class of phenolic solvents which have negative deviations from ideal mixing for the ethanol/solvent binary. Negative deviations from ideal mixing for the ethanol/solvent binary are accompanied by attractive forces instead of repulsive forces. Thus, the phenolic agents are highly suitable for the extraction or extractive distillation of solutions comprised of alcohol and water, especially solutions of ethanol and water.

BRIEF DESCRIPTION OF THE INVENTION

The present invention relates to a process which comprises the steps:

(a) distilling a feed mixture comprising water and an alcohol with an extractive solvent comprising a substituted or unsubstituted phenol of at least six carbon atoms to produce a first overhead vapor stream consisting essentially of water and a first bottoms liquid stream consisting essentially of said alcohol and said extractive solvent; and (b) distilling said liquid stream to produce a second overhead vapor stream consisting essentially of said alcohol and a second bottoms liquid stream consisting essentially of said extractive solvent; wherein said alcohol comprises a low molecular weight alcohol having 2 to 4 carbons.

DETAILED DESCRIPTION OF THE INVENTION

Figure 1:
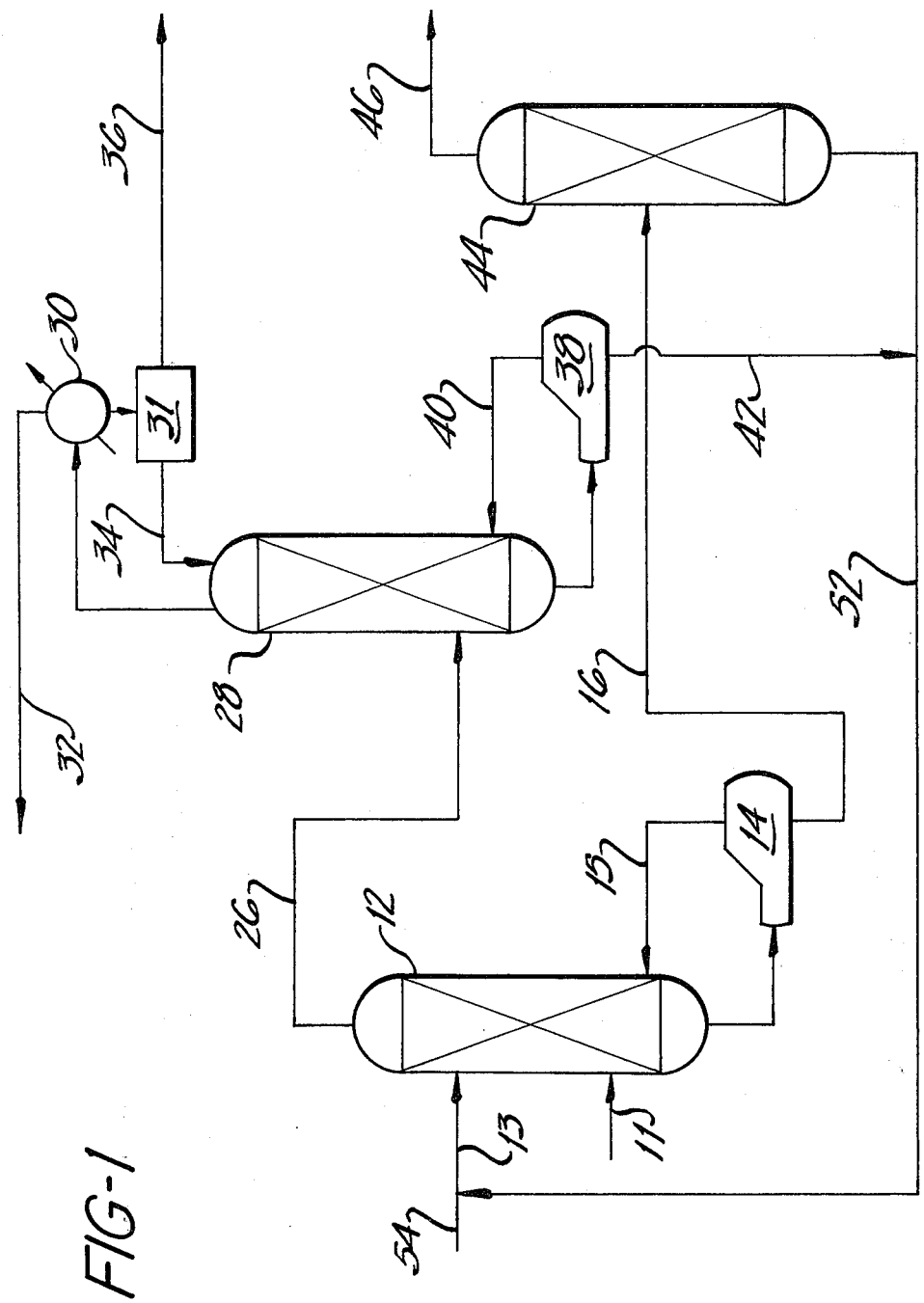
FIG. 1 is a schematic view of the extractive distillation process of this invention.

In accordance with the present invention, a process is disclosed for the separation of alcohols from aqueous solutions. The novel process involves extraction of the alcohol from an aqueous solution by extractive distillation. An alternate means for practicing this invention includes a conventional extraction followed by an extractive distillation. The novel process utilizes solvents which have not previously been employed in the separation of alcohols from aqueous solutions. Additionally, the process includes novel modifications of standard extraction distillation procedures. The usefulness of this invention resides in the fact that the process is a more cost effective method for separating alcohols from aqueous solutions than are existing processes which accomplish this function.

Existing processes for the extraction, extractive distillation and azeotropic distillation of alcohol-water mixtures are based on the knowledge of positive deviations from ideal mixing exhibited by the binary combinations of alcohol/water, water/solvent and alcohol/solvent. The existing processes utilize extractive solvents which result in a positive deviation from ideal mixing for the alcohol/solvent binary which is lower than the positive deviation from ideal mixing for the alcohol/water and water/solvent binaries.

We have discovered that certain alcohol/solvent binary mixtures do not exhibit positive deviations from ideal mixing and accompanying undesirable repulsive forces. The novel binary mixtures of the alcohols and the solvents of this invention exhibit negative deviations from ideal mixing. Negative deviations from ideal mixing result in strong attractions between the extractive solvent and the alcohol. Furthermore, the binary mixture of the same solvent and water has a strong positive deviation manifested by repulsive forces. This combination of mixing phenomena enables one to separate alcohols from water more easily and less expensively than previously thought possible.

The attractive forces stemming from the negative deviations from ideal mixing of the alcohol/solvent binaries result in their mixtures having lower vapor pressures than otherwise would result if their mixture exhibited positive deviations from ideal mixing. Thus, the relative volatility between the alcohol and water is reversed with sufficient quantities of the extractive solvent. More particularly, the alcohol becomes less volatile due to the negative deviation behavior of the extractive solvent and the alcohol.

The process of this invention is suitable for the separation of low molecular weight alcohols having 2 to 4 carbons from their mixtures with water. Illustrative examples of alcohols which may be separated from their mixtures with water include ethanol, n-propanol, isopropanol, n-butanol and isobutanol. In many preferred embodiments of this invention, ethanol is separated from ethanol-water mixtures in accordance with the practice of this invention.

Extractive solvents which exhibit negative deviations from ideal mixing with alcohols, and which are thus suitable for the practice of this invention include phenols having at least 6 carbons and a boiling point between about 180° C. and about 350° C. Phenols falling within these criteria include substituted or unsubstituted phenols including cresols, xylenols or the like and mixtures thereof. In many preferred embodiments of this invention monocyclic phenols substituted by at least one linear or branched alkyl group having 1 to 6 carbon atoms, cycloalkyl group having 5 to 10 carbon atoms, aryl group having 6 to 18 carbon atoms, or phenols substituted by a combination of said groups may be employed as extractive solvents. All said phenols may have one or more hydrogen atoms replaced by a halogen such as chlorine, bromine, fluorine or iodine. Illustrative examples of preferred extractive solvents include any isomer or mixtures of cresol, xylenol, trimethyl phenol, ethyl phenol, propyl phenol, diethyl phenol, diisopropyl phenol, cumyl phenol, phenyl phenol, cyclohexyl phenol or the like with cyclohexyl phenol and phenyl phenol being especially preferred. In many especially preferred embodiments of this invention extractive solvents having at least 6 carbon atoms and a boiling point between about 225° C. and 340° C. are employed. Illustrative examples of especially preferred solvents include 2-phenyl-phenol, cumyl phenol, diisopropyl phenol or mixtures thereof.

The extractive phenolic solvent may also contain minor proportions of other phenols having at least six carbon atoms. Many of these phenols are commonly present in various industrial processes. For example, cresols and xylenols having a normal boiling point between about 200° C. and about 222° C. are major constituents of a coal tar distillate. Additionally, cresols and xylenols are often found in some petroleum acid stocks such as those recovered from acidifying the "extract" from caustic extraction of carbolic oil. Other phenols commonly found in industrial streams include the cumyl phenols which are produced as by-products in the manufacturing of phenol from cumene. Other similar examples include cyclohexyl and phenyl phenols which are present in the residue from the recovery of products of phenol hydrogenation.

The extractive distillation process of the present invention involves the distillation of alcohol-water mixtures in the presence of added solvent. Typically, the alcohol-water mixture is fed to an intermediate point of a tray or a packed column, the solvent is fed to a higher tray, and suitable processing rates, temperature and pressure conditions and reflux ratios are employed. The overheads of this first distillation contains water, with very small amounts of alcohol and solvent, preferably at least 99.9 weight percent water. The bottoms contains solvent and alcohol, preferably with minimal amounts or with no water; the amount of water in the bottoms can be controlled by varying the conditions of the process, the equipment setup and/or the solvent to feed ratios. Subsequent distillation of these bottoms (preferably fractional distillation) produces a second overhead high in alcohol concentration (preferably at least 96 weight percent and more preferably at least 99.9 weight percent alcohol). When the extractive distillation solvent is one of the alkyl, aryl or cycloalkyl phenols listed above, the second overhead will consist essentially of only alcohol and minor amounts of water. Both distillation steps may be conducted at atmospheric pressure, but it is preferred to operate the second distillation step or parts thereof at below atmospheric pressure, for example between about 1 and about 50 kPa. Regardless of the pressure chosen for the second step, alcohol concentrations obtainable will exceed the proportion of alcohol in the alcohol-water azeotrope at the distillation pressure, and thus be greater than could be achieved by simply distilling the feed mixture in a conventional fashion at this pressure with a large number of effective trays or equivalents thereof and with high reflux ratios.

The first overhead vapor stream comprising mainly water vapor having traces of solvent may be condensed with reflux and treated in conventional manner to remove the traces of solvent. Preferably, however, the first overhead is further distilled in another column to produce a second overhead stream which is essentially pure water and a bottoms stream which is rich with solvent. Depending upon the conditions selected, the bottoms for this distillation may be comprised of a single phase rich in solvent or two separate water and solvent phases. When two phases are present, the bottoms may be passed to a reboiler where water vapor is produced which may be returned to the second distillation column, and liquid consisting essentially of extractive solvent is produced which may be recycled for use in the extractive distillation step of this invention.

Another embodiment of this invention involves a modification of the process that results in significant energy savings. The energy input for this invention may be reduced by only partially condensing and refluxing the overhead stream from the first distillation (second distillation if the first overhead is further distilled). The major portion of said overhead stream, which is virtually pure steam, may be recompressed and condensed in one of the reboilers of the distillation system. By implementing these steps, the latent heat of condensation may be recovered.

The feed mixture of either the extraction process of the extractive distillation process may contain other materials in addition to ethanol and water. It is preferred, however, to feed mixtures such as are generated by distilling fermentation mixtures in a "beer still" which produces a product consisting essentially of water and ethanol. Minor impurities which may be present include "fusel oil" (amyl alcohols, aldehydes and similar materials) which is present in the extract in the present extraction process and in the second bottoms in the extractive distillation process. In either case, fusel oil and similar contaminants may be recovered together with the alcohol as part of the overhead from the recovery (second) distillation in the event that the alcohol thus produced is intended for use as fuel. Alternately, they may be bled from the system by subjecting the solvent or a portion thereof to a process such as further low pressure distillation for reducing the impurity concentration in the solvent and recovering these organic compounds if such is desired.

In the extraction process of the present invention, mixtures of alcohol and water in compositions such as 8-70 (preferably 20-60) weight percent alcohol and 30-92 (preferably 40-80) weight percent water are contacted with the extractant in a single stage or multiple stages. Extracting apparatus preferably are operated in a manner of counter-current flow (e.g. through a packed or tray column or any extracting device).

The raffinate contains water with relatively little alcohol, depending upon the solvent, effective number of stages, ratios of mixture to extractant, temperature and other conditions. A small quantity of solvent may be found in the raffinate. The extract will contain solvent and alcohol with relatively little water and in some conditions practically none. Alcohol can be separated from the solvent by distillation with the solvent recycled for reuse.

FIG. 1 illustrates the extractive distillation process of this invention for the separation of ethanol from water. An ethanol-water mixture (e.g. 50:50 mixture by weight) is fed in stream 11 to a packed or tray extractive distillation column 12. At a point above the point where stream 11 is fed, an extractive solvent stream 13 (2,2-diisopropyl phenol) is fed to column 12, at a selected temperature. The bottoms of the column are heated by direct or indirect steam heating or other heating means in reboiler 14 with a portion returned in stream 15 and a portion fed forward in stream 16. The overheads from extractive distillation column 12 exits column 12 into stream 26 and passes via stream 26 into distillation column 28 which functions as a rectifier. The overheads from distillation column 28 are partially condensed in condenser 30 with the condensate being collected in vessel 31 (which may include means for phase separation), with a portion (including especially any separate organic layer) recycled in stream 34 to near the top of column 28. Essentially, pure water passes from the system via stream 36. The non-condensed portion (which is essentially pure steam) may be passed via stream 32 to a compressor and then a reboiler to capture the latent heat of condensation as described hereinbefore. The bottoms (comprising mainly extractive solvent) of distillation column 28 are heated by direct or indirect steam heating or other heating means in reboiler 38. A small amount of water vapor is returned to distillation column 28 via stream 40, and a liquid extractive solvent portion passes via stream 42 to stream 52 where it passes to stream 13 for recycling in the process of this invention.

Stream 16 comprising extractive solvent and ethanol passes to distillation column 44 where an overhead vapor comprising above about 96% ethanol and preferably above about 99% ethanol is withdrawn and passed into stream 46. Distillation column 44 preferably operates at subatmospheric pressure. The bottoms 52 comprising primarily extractive solvent may be passed to stream 13 for recycling. It should be appreciated that distillation column 44 is equipped with a condenser for partial reflux, and that bottoms stream 52 is fed to a reboiler prior to recycling. The reboiler produces a small amount of ethanol vapor which is returned to distillation column 44.

It is contemplated to use a variety of standard engineering devices known to the distillation art in practicing the present invention. Thus, for example, streams 36, 46 and 52 may be passed, as appropriate, in heat exchange with other streams for cooling or heating, preferably prior to passage in heat exchange with cooling water, steam or other process streams. Furthermore, if the present process is combined with operation of a "beer still" to produce stream 11, heat exchanges between various streams in the present process and streams of the "beer still" are also contemplated.

The solvent in stream 52 may be cooled and mixed with makeup solvent 54 whenever the latter is required, and returned into column 12 as stream 13 or the solvent, or any portion thereof, may be treated (e.g. by vacuum distillation) to remove any built up fusel oil or other impurities.

Figure 2:
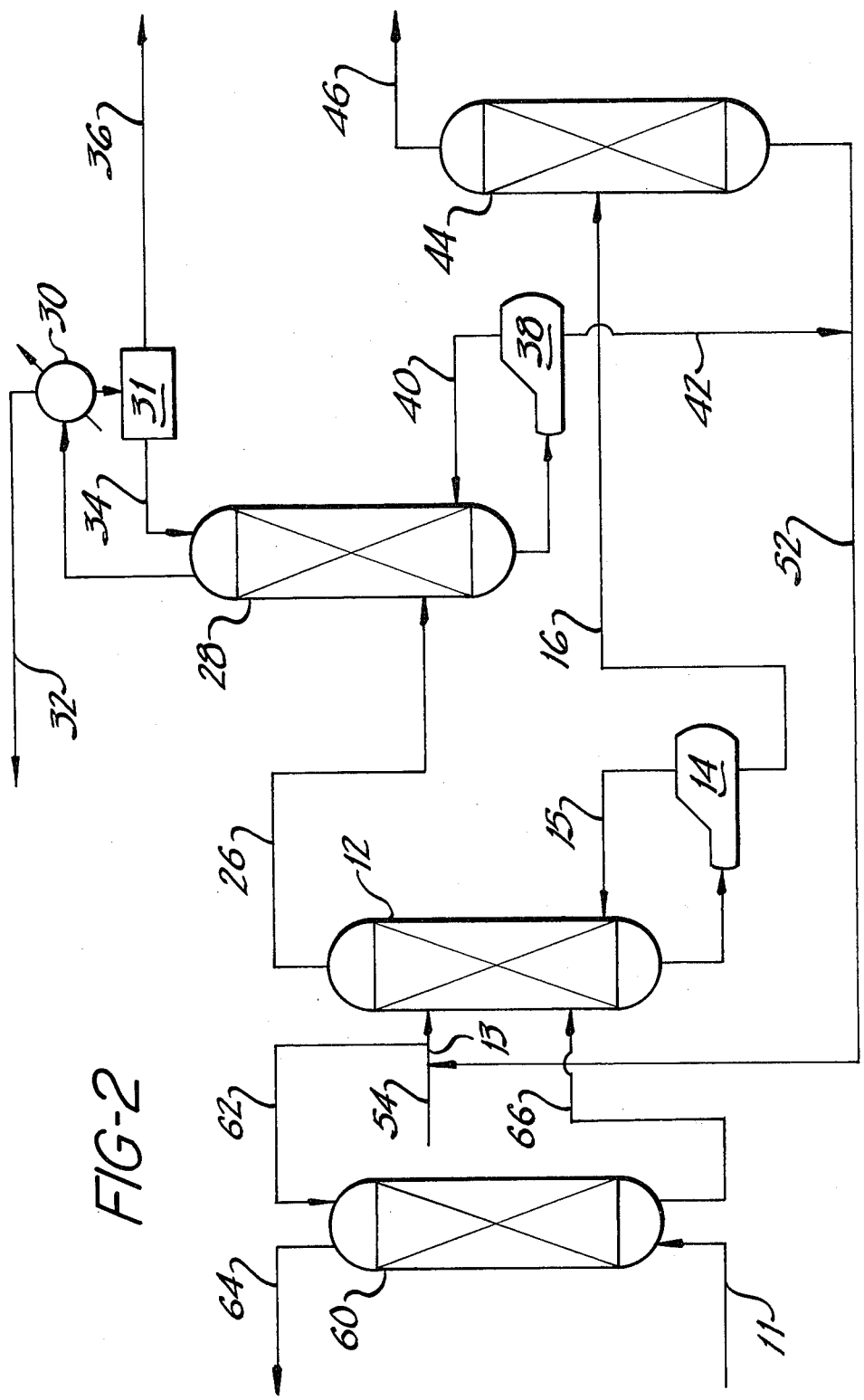
FIG. 2 is a schematic view of the extractive distillation process of this invention in combination with a conventional extraction.

FIG. 2 illustrates a variation of the combination of the extractive method of the present invention with the extractive distillation method of the present invention. Feed mixture 11 (e.g. 50:50 ethanol-water) is fed to the bottom of packed column 60 where it is passed in countercurrent contact with an extractive solvent fed into the top of the column in stream 62. The raffinate containing water and minor organic content is removed from the top of column 60 as stream 64. The extract containing mainly solvent and ethanol, with some water content, is removed from the bottom of the extraction column 60 in stream 66 and fed to distillation column 12. Column 12 and the remainder of the system is operated as described above in the variation of this invention illustrated in FIG. 1. The water removed in stream 36 of FIG. 2 is reduced in quantity compared to stream 36 of FIG. 1 by approximately the amount of water removed in stream 64. Accordingly, this embodiment is especially suitable with feed mixtures 11 having more water than ethanol. The feed of the solvent in stream 62 should be sufficiently high compared to ethanol in stream 11 for the density of extract in stream 66 to remain greater than the density of ethanol-water in streams 11 and 64.

The bottoms 16 are fed from reboiler 14 of column 12 into column 44, which preferably can be and is operated at subatmospheric pressure. Overhead 46 is rich in ethanol while bottoms 52 is very rich in solvent. The solvent in stream 52 may be recycled into streams 62 and 13, optionally after a separate distillation to purge fusel oil.

To practice a simple alcohol extraction recovery process, one need only feed stream 66 in FIG. 2 directly to column 44, providing an overhead which is rich in ethanol and a bottoms for recycle which is mainly solvent. In such a scheme, both reflux and reboil are employed on column 44 in conventional fashion.

EXAMPLE 1

A mixture containing 12 grams ethanol and 10 grams water was mixed with 24 grams of 2-phenyl-phenol at 22° C. under atmospheric pressure. After agitation, the two liquid phases were allowed to settle. Samples were taken and analyzed. The results are shown in Table 1 as Experiment A in terms of distribution coefficients and selectivity for ethanol.

Additional water was added to the mixture which resulted from experiment A, and the two liquid phases were allowed to settle. Samples were taken and analyzed. The results are shown in Table 1 as Experiment B in terms of distribution coefficents and selectivity for ethanol.

In Table 1, the distribution coefficient for ethanol ($D_E$) is defined as the ratio of the solubility of ethanol in mols/liter of solvent (2-phenyl-phenol) to the solubility of ethanol in mols/liter of water. The distribution coefficient for water ($D_H$) is defined likewise. The selectivity for ethanol ($S_E$) of 2-phenyl-phenol is the ratio of $D_E$ to $D_H$.

TABLE I

| Experiment # | Ethanol | Water | 2-phenyl-phenol | $D_E$ | $D_H$ | $S_E$ |
|---|---|---|---|---|---|---|
| A. Upper | 13.596 | 86.392 | 0.0118 | 1.16 | 0.081 | 11.7 |
| Lower | 45.00 | 24.56 | 30.344 | | | |
| B. Upper | 7.168 | 92.792 | 0.040 | 0.94 | 0.036 | 21.4 |
| Lower | 29.28 | 17.665 | 53.055 | | | |

EXAMPLE 2

The process of this invention was demonstrated using a computer simulation of the extractive distillation and extraction process end of the invention. A distillation program which is part of Allied Corporation's Process Analysis Group Program Library was used for our process simulations. Basic physical properties of the components used in our process and described forthwith in this example were entered into the program for heat balances, material balances and vapor-liquid equilibrium calculations.

The physical properties used for ethanol, water and the solvent (90 mol percent 2-phenyl-phenol and 10 mol percent cumyl phenol) in this example were vapor pressures, molecular weights, heat capacities, enthalpy of vaporation and molar volumes. The Antoine Equation with the standard three coefficients was used as the vapor pressure model. Data for the system was obtained from "The Properties of Gases and Liquids" by R. C. Reid, J. M. Prausnitz and T. K. Sherwood. Vapor pressure for the solvent was obtained from "Vapor Pressure of Organic Compounds" by T. Earl Jordan, pp. 203–219.

The development of a vapor-liquid equilibrium, VLE, model used in the distillation program will now be described. The Redlick-Kister equation of state was used for the vapor-liquid equilibrium of the ethanol/water/solvent (90 mol percent 2-phenyl-phenol and 10 mol percent cumyl phenol). The Redlick-Kister coefficients for the ethanol/solvent and water/solvent mixtures were obtained by correlation and analogy of group behavior between cyclohexanol/phenol and water/phenol systems from D. R. Cora "Vapor-Liquid Equilibria in Binary and Ternary Systems-Cyclohexanol-Phenol, Cyclohexanone-Cyclohexanol and Cyclohexanone-Phenol-Cyclohexanol" Jour. Chem. Eng. Data, 5, 282, (1960) and R. A. Murogova, Zhur Prikl, Khim 45, 824, (1972). This data and the activity coefficient at infinite dilution data were obtained from extrapolation of the distribution coefficients experimentally obtained in Example 1. Activity coefficients at infinite dilution for ethanol/water were obtained through the literature from J. Gmehling and V. Onken "Vapor-Liquid Equilibrium Data Collection, Aqueous-Organic Systems" Vol 1 part 1 pp. 150–196. Using the activity coefficients at infinite dilution, we correlated Redlick-Kister parameters using standard techniques in Engineering Thermodynamics.

A computer-laboratory simulation was performed using the described VLE model. This simulation will now be described.

A liquid mixture stream of 22.2 mol percent ethanol and 77.8 mol percent water called "Feed #1" was fed continuously at a rate of 36 mol/hr onto the fourth tray above the reboiler of a distillation column having fifty-three theoretical trays with a reboiler and condenser. Simultaneously with the introduction of "Feed 1", another stream called herein "Feed 2" was fed continuously at the rate of 60 mol/hr onto the top tray of the distillation assembly. Feed 2 contained 90 mol percent 2-phenyl-phenol and 10 mol percent cumyl phenol (primarily the para isomer). The system was operated at 760 Torr (101.33 kPa). The bottoms stream was continuously withdrawn. The bottoms contained 11.76 mol percent ethanol and 0.0006 mol percent water. The remainder of the bottoms comprised extractive solvent. Ethanol was not detectable in the overhead vapor. The overhead vapor was distilled once more. This was accomplished by feeding the vapor onto the fourth tray above a reboiler of a distillation column having eight theoretical trays with a condenser. The second distillation of the overhead vapor from the first extractive distillation was run under reflux. A reflux ratio of 0.2:1 was employed for the second distillation. The overhead condensate from the second distillation was essentially pure water and contained no detectable 2-phenyl-phenol. The bottoms from the second distillation of the overhead vapor contained 82.69 mol percent 2-phenyl-phenol and 17.31 mol percent water. Utilizing the information obtained in Example 1, we determined that upon cooling, the bottoms will consist of two phases. The lower organic phase will consist of 91.5 mol percent 2-phenyl-phenol and 8.5 mol percent water. The upper aqueous phase will consist of 99.97 mol percent water and 0.03 mol percent 2-phenyl-phenol.

Simultaneously, with the treatment of the overhead vapor from the extractive distillation column, the bottoms comprising primarily extractive solvent and ethanol from the extractive distillation column was fed onto the sixth tray of a distillation column having eighteen theoretical plates, a reboiler and a condenser. Distillation of the bottoms was conducted under reflux with a reflux ratio of 0.4:1 being employed. The overhead vapor from distillation of the bottoms contained 99.64 mol percent ethanol and 0.36 mol percent water. The liquid bottoms produced by this distillation contained 99.95 mol percent extractive solvent and 0.05 mol percent ethanol.

The results of this example illustrate that essentially pure ethanol and water can be separated from an ethanol-water mixture by employing the extractive distillation process of this invention.

We claim:

1. A process for the concentration of an alcohol which comprises:
   (a) distilling a feed mixture comprising water and an alcohol with at least one extractive solvent comprising a substituted or unsubstituted phenol having at least 6 carbon atoms and a boiling point between about 180° C. and about 350° C. to produce a first overhead vapor stream consisting essentially of water and a first bottoms liquid stream consisting essentially of said alcohol and said extractive solvent; and
   (b) distilling said liquid bottoms stream to produce a second overhead vapor stream consisting essentially of said alcohol and a second bottoms liquid stream consisting essentially of said extractive solvent; wherein said alcohol comprises a low molecular weight alcohol having 2 to 4 carbon atoms.

2. A process according to claim 1 wherein said alcohol is ethanol.

3. A process according to claim 2 wherein said extractive solvent is selected from the group consisting of 2-phenyl-phenol, cumyl phenol, diisopropyl phenol or mixtures thereof.

4. A process according to claim 3 wherein said extractive solvent is 2-phenyl-phenol.

5. A process according to claim 3 wherein said extractive solvent comprises a mixture of 2-phenyl-phenol and cumyl phenol.

6. A process according to claim 1 or 2 or 3 wherein said feed mixture contains about 8–70 weight percent alcohol and about 30–92 weight percent water.

7. The method of claim 6 wherein said feed mixture contains about 40–60 weight percent alcohol and about 40–60 weight percent water.

8. The method of claim 6 wherein the first overheads stream contains at least about 90 weight percent water and the second overhead stream contains at least about 95 weight percent alcohol.

9. The method of claim 8 wherein the second overhead stream contains a greater alcohol weight proportion than the alcohol weight proportion in the alcohol-water azeotrope at the operating pressure of the distillation step b.

10. The method of claim 8 wherein each distillation step is conducted at atmospheric pressure.

11. The method of claim 8 wherein said distillation step (a) is conducted at atmospheric pressure and said distillation step (b) is conducted below atmospheric pressure.

12. A process according to claim 1 wherein said feed mixture is the extract from an extraction of a mixture comprising said low molecular weight alcohol and water with said extractive solvent wherein said extraction produces a raffinate comprising water and an extract which is the feed mixture for said distilling step (a).

13. A process according to claim 12 wherein said alcohol is ethanol.

14. A process according to claim 13 wherein said extractive solvent is selected from the group consisting of 2-phenyl-phenol, cumyl phenol, diisopropyl phenol or mixtures thereof.

15. A process according to claim 14 wherein said extractive solvent is 2-phenyl-phenol.

16. A process according to claim 14 wherein said extractive solvent comprises a mixture of 2-phenyl-phenol and cumyl phenol.

* * * * *